United States Patent [19]
Brauner

[11] Patent Number: 5,803,078
[45] Date of Patent: Sep. 8, 1998

[54] METHODS AND APPARATUS FOR INTRAPULMONARY THERAPY AND DRUG ADMINISTRATION

[76] Inventor: Mark E. Brauner, 722 N. Indiana Ave., Bloomington, Ind. 47408

[21] Appl. No.: 451,733

[22] Filed: May 26, 1995

Related U.S. Application Data

[63] Continuation-in-part of Ser. No. 282,900, Jul. 29, 1994, abandoned, which is a continuation-in-part of Ser. No. 239,241, May 6, 1994, abandoned.

[51] Int. Cl.$^6$ .................................................. A61M 16/00
[52] U.S. Cl. .................... 124/207.14; 128/911; 128/912; 128/200.14
[58] Field of Search ............................... 128/912, 200.26, 128/207.14, 207.15, 207.16, 200.14, 200.18, 200.21, 200.23, 203.12, 911; 604/171

[56] References Cited

U.S. PATENT DOCUMENTS

| | | |
|---|---|---|
| 2,638,096 | 3/1953 | Waldhaus . |
| 3,788,326 | 1/1974 | Jacobs . |
| 4,327,721 | 5/1982 | Goldin et al. . |
| 4,584,998 | 4/1986 | McGrail . |
| 4,646,733 | 3/1987 | Stroh et al. . |
| 4,669,463 | 6/1987 | McConnell . |
| 4,739,756 | 4/1988 | Horn . |
| 4,805,609 | 2/1989 | Roberts . |
| 4,881,542 | 11/1989 | Schmidt et al. .................... 128/207.14 |
| 4,886,055 | 12/1989 | Hoppough . |
| 4,955,375 | 9/1990 | Martinez . |
| 5,012,804 | 5/1991 | Foley . |
| 5,029,580 | 7/1991 | Radford . |
| 5,031,613 | 7/1991 | Smith . |
| 5,062,423 | 11/1991 | Matson . |
| 5,072,726 | 12/1991 | Mazloomdoost . |
| 5,078,131 | 1/1992 | Foley . |
| 5,116,088 | 5/1992 | Bird . |
| 5,119,807 | 6/1992 | Roberts . |
| 5,146,916 | 9/1992 | Catalini . |

(List continued on next page.)

FOREIGN PATENT DOCUMENTS

| | | |
|---|---|---|
| 0445502 | 1/1991 | European Pat. Off. . |
| 0487155 | 9/1991 | European Pat. Off. . |
| 0453234 | 10/1991 | European Pat. Off. . |
| 185442 | 8/1966 | U.S.S.R. . |
| 812296 | 3/1979 | U.S.S.R. . |
| 2098485 | 11/1982 | United Kingdom . |

OTHER PUBLICATIONS

Product Brochure–"Endo–Ject by Autovage", manufactured by Autovage, 1631 Citation Drive, Library, PA (date unknown).

Product Brochure–"Administer RX and CPR simultaneously with EMT", manufactured by Mallinckrodt Medical, Inc., St. Louis, MO, Jan. 1993.

*Primary Examiner*—Aaron J. Lewis
*Assistant Examiner*—William J. Deane, Jr.
*Attorney, Agent, or Firm*—Townsend and Townsend and Crew

[57] ABSTRACT

An endotracheal catheter assembly and method for deep intrapulmonary, aerosol delivery of liquid drugs and other liquid therapeutic agents. The invention can deliver a bolus dose of liquid drugs into the lungs of a patient which is at least bioequivalent in terms of physiological effect to a similar drug dose delivered intravenously. The catheter assembly includes a first, gas-bearing tube and a second, liquid bearing tube, preferably concentrically nested within the gas-bearing tube. The tubes are inserted in an airway of the patient, preferably by threading the tubes into a lumen of an endotracheal tube, to position a terminal nozzle formed by distal tips of the tubes near a carina of the patient. At the nozzle, the lumen of the first tube has a comparative cross-sectional area relative to that of the second tube's lumen of between about 0.4:1.0 and 4.0:1.0. In operation, high velocity gas is forced from the first tube and impacts liquid expelled from the second tube at a high velocity gas/liquid interface, deforming the liquid into an aerosol and propelling it deep within the lungs of the patient.

17 Claims, 5 Drawing Sheets

U.S. PATENT DOCUMENTS

| | | | |
|---|---|---|---|
| 5,152,277 | 10/1992 | Honda et al. | 604/171 |
| 5,178,138 | 1/1993 | Walstron . | |
| 5,261,892 | 11/1993 | Bertaud et al. | 604/171 |
| 5,287,847 | 2/1994 | Piper . | |
| 5,287,850 | 2/1994 | Haber . | |
| 5,313,939 | 5/1994 | Gonzalez . | |
| 5,333,607 | 8/1994 | Kee et al. | 604/171 |
| 5,372,131 | 12/1994 | Heinen | 128/207.15 |
| 5,433,195 | 7/1995 | Kee et al. | 604/171 |
| 5,499,625 | 3/1996 | Frass et al. | 128/207.15 |

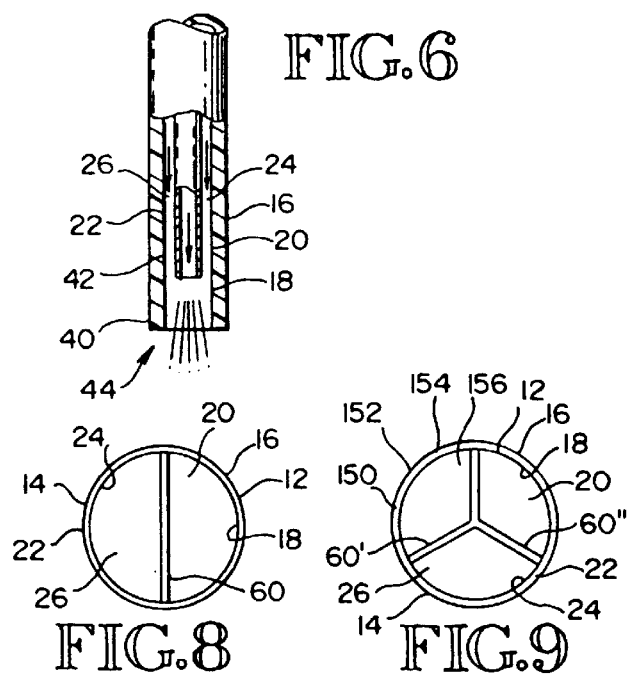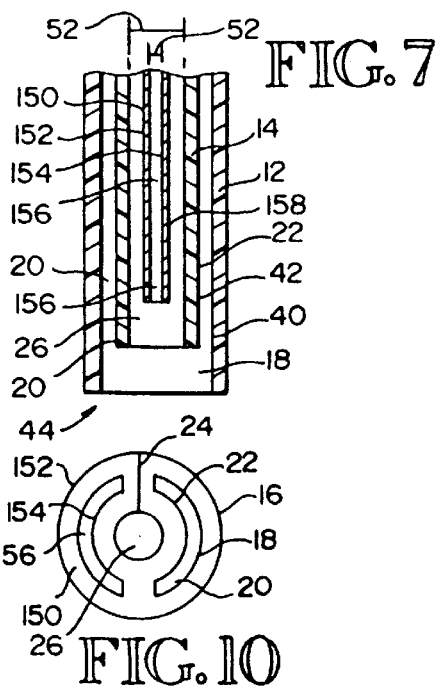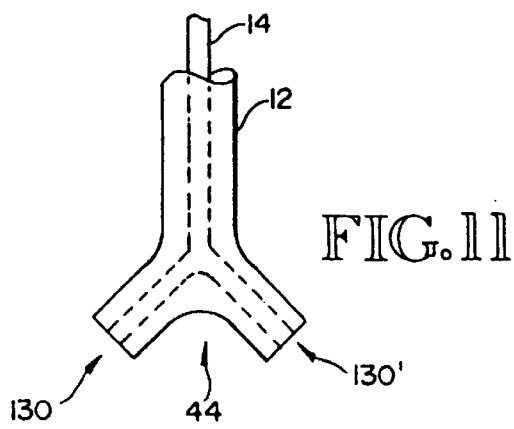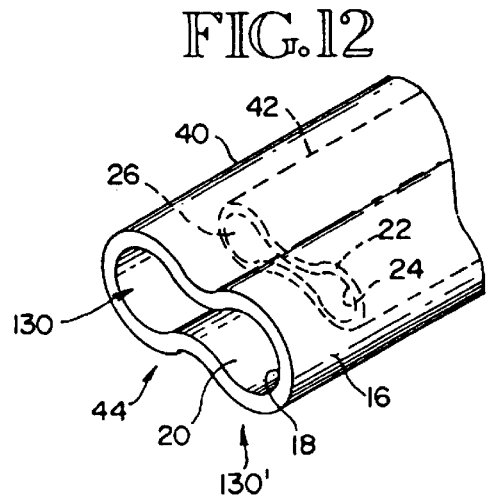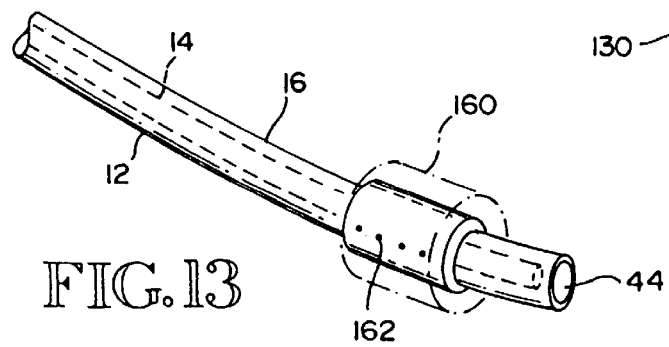

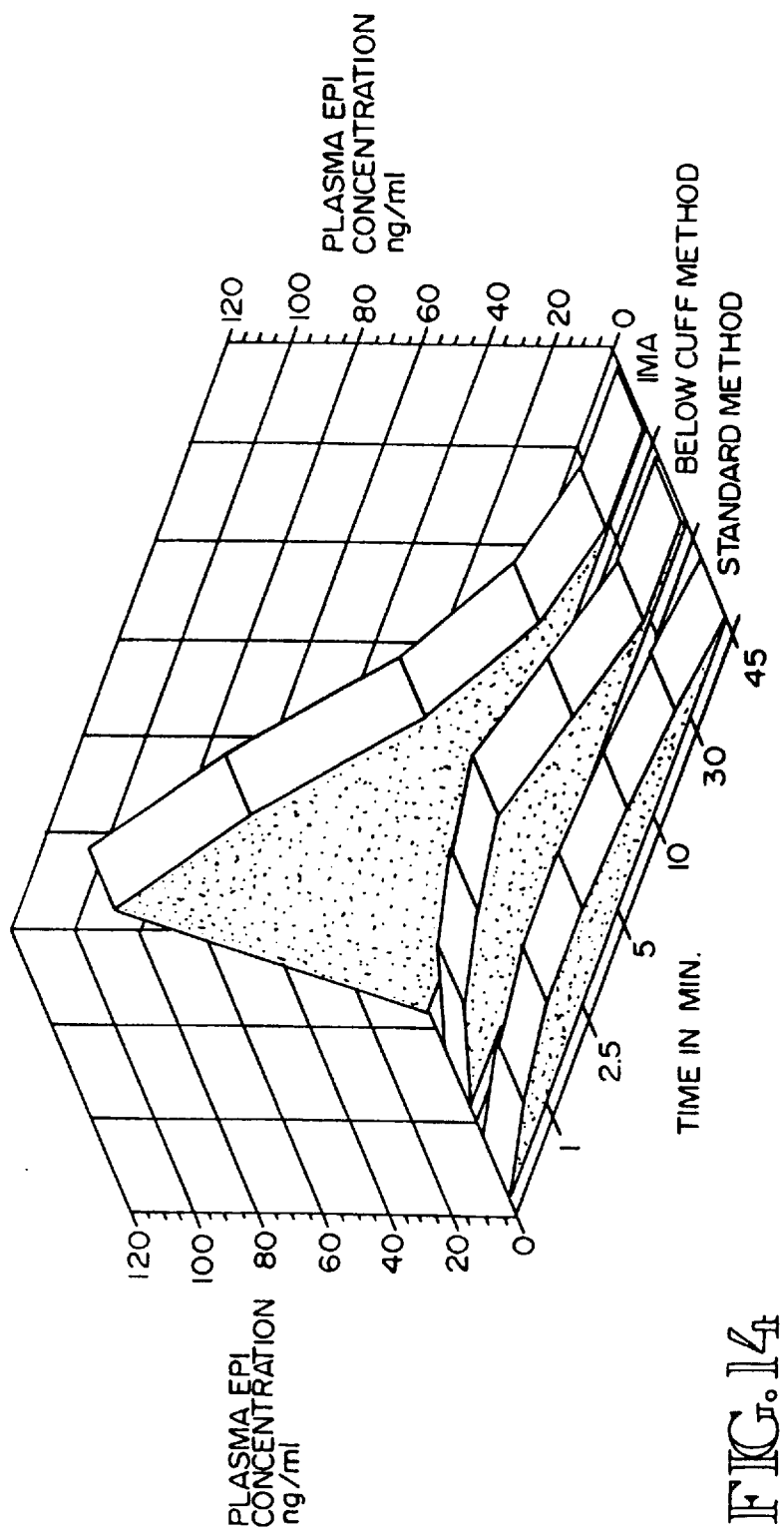

METHODS AND APPARATUS FOR INTRAPULMONARY THERAPY AND DRUG ADMINISTRATION

RELATED APPLICATIONS

This application is a continuation-in-part of application Ser. No. 08/282,900, filed Jul. 29, 1994 now abandoned as a continuation-in-part of an original parent application Ser. No. 08/239,241, filed May 6, 1994 now abandoned.

TECHNICAL FIELD

The invention relates to methods and devices for administering drugs and other treatments via the respiratory system of a patient. More specifically, the invention relates to methods and devices for direct delivery of liquid drugs to the pulmonary tissues of a patient.

BACKGROUND OF THE INVENTION

Medical care costs in the United States have reduced the nation's gross national product dramatically. As a result, medical care has become one of the foremost topics on the national agenda. Of all types of care, emergency care, with its heavy resource demand and its stop-gap nature, is the most expensive. In addition, the timeliness and effectiveness of emergency care is a primary factor in determining emergency patient survival and limiting their need for long-term hospitalization. Accordingly, new technologies which can improve the accessibility, quality and cost of emergency care will have significant beneficial impacts throughout our medical care system.

Perhaps the most important requirement for successful emergency care is the need for rapid and effective administration of life saving medications. Prompt delivery of medication is a key factor in the survival and recovery of cardiac arrest patients, among a variety of other emergency patient classes. Unfortunately, rapid administration of medications is problematic due to poor intravenous access in many patients, including cardiac arrest victims, diabetics and intravenous drug users. In these patients, drug delivery to the central circulation may be difficult or impossible, so that an alternate mode of medication delivery becomes a necessity. Furthermore, even when intravenous drug delivery is available in emergency situations, suitable alternative methods of delivery may be desired. In particular, intravenous drug delivery greatly increases the risk of exposure of medical workers to highly infectious, blood-borne diseases, such as AIDS, hepatitis and tuberculosis. In addition, intravenous administration of drugs requires that the medication must travel approximately 70 cm in the bloodstream before it can reach the heart and be pumped to the peripheral organs and tissues. Moreover, intravenous administration of some important emergency drug agents, for example concentrated alpha-1 agonist for cardiac arrest patients, may also be problematic due to local vasoconstriction caused by the drug. Accordingly, methods of drug delivery which do not require intravenous access, and which deliver medication via a more direct circulatory route compared to peripheral, intravenous delivery, are desirable in a variety of emergency and clinical care situations.

Despite the widely recognized need for alternative modes of drug delivery to overcome the problems of intravenous drug administration, efforts to satisfy this need have met with limited success. Among these efforts, previous studies have focused on the potential benefits of intrapulmonary drug administration for emergency care. These potential benefits include the direct accessibility of pulmonary tissues without the need for intravenous access, the large surface area and extensive vascularization of the pulmonary tissues for drug absorption, and the close circulatory path between the heart and lungs for rapid distribution of drugs to the periphery. However, even though these potential benefits have long been recognized, intrapulmonary drug delivery has remained problematic for a variety of reasons.

Previous efforts to develop intrapulmonary drug delivery technology have been directed to three main types of apparatus and methods. One of these types of apparatus is exemplified by the coupled external nebulizers, shown in U.S. Pat. Nos. 5,012,804 and 5,078,131, issued to M. P. Foley on May 7, 1991 and Jan. 7, 1992, respectively, in U.S. Pat. Nos. 4,805,609 and 5,119,807, issued to J. A. Roberts et al. on Feb. 21, 1989 and Jun. 9, 1992, respectively, and in U.S. Pat. No. 5,072,726, issued to Mazloomdoost et al. on Dec. 17, 1991. Each of these examples uses an external nebulizer, similar in function to a conventional, hand-held nebulizer used by asthma patients, to produce a spray of liquid medication particles. The nebulizer is coupled in-line to an artificial ventilation unit, and the spray of medication is entrained in a flow of ventilation gas flowing into the patient via a standard endotracheal tube.

Coupled external nebulizers suffer a variety of important drawbacks, and are generally unsatisfactory for intrapulmonary drug delivery. One fundamental drawback of the devices is that they rely on external nebulization of liquid medication into a spray, which is introduced into the ventilation path outside the patient's body. Because of this limitation, the spray of liquid medication must flow a considerable distance through the endotracheal tube, which results in a substantial portion of the medication being deposited on the walls of the endotracheal tube. The deposited medication drips from the distal tip of the endotracheal tube onto the tracheal or bronchial surfaces, and does not effectively reach the respiratory surfaces of the lungs for absorption into the pulmonary circulation. In addition, the droplets of medication which drip from the distal tip of the endotracheal tube can irritate the tracheal and bronchial tissues, because the medication is not delivered in a uniform pattern over a large surface area of tissue. This drawback is exacerbated by the fact that most coupled external nebulizers are used in conjunction with Normal Volume Cycled (NVC) ventilation, which uses cyclic, low pressure ventilation achieved manually or by an NVC ventilator. Such ventilation (from a respirator or an ambu bag) was originally designed to gently inflate the lungs, and is not adapted for liquid spray propulsion. Because the ventilation uses intermittent, low velocity gas flow, the ventilating gas stream is inefficient for propelling liquid particles deep into the pulmonary passageways.

At least one coupled external nebulizer has been developed which reportedly provides true nebulization of liquid medications. U.S. Pat. No. 5,072,726, issued to Mazloomdoost, describes an external medication "atomizer" which connects to an endotracheal tube and generates a fine particulate mist having particle sizes in the range of several $\mu$ in diameter. More specifically, the device of Mazloomdoost uses a high pressure gas supply needle adjacent to, and oriented at a 90 degree angle with respect to, a liquid anesthetic supply needle containing a volatile liquid anesthetic, such as enflurane. The gas and anesthetic valves are mounted in a housing coupled to a High Frequency Jet Ventilation (HFJV) unit. The high pressure gas needle is directed at the tip of the anesthetic supply needle, and creates a negative pressure sufficient to draw anesthetic from the needle into the housing, where the high pressure gas impinges on the liquid and disintegrates the medication into an aerosol. Because of the effective nebulization caused by the high pressure gas impinging on the expelled liquid medication in the housing, and because of the volatility of the liquid anesthetics used, the Mazloomdoost device actually causes evaporation of the nebulized liquid, i.e. from an aerosol to a full gaseous state. Consequently, Mazloomdoost overcomes the problems of other coupled external nebulizers, because the nebulized-then-vaporized medication cannot become deposited within the endotracheal tube, or in the shallow pulmonary passages (i.e. trachea, carina or bronchi). However, less volatile drugs may remain in an aerosol state after nebulization. Consequently, if evaporation is not achieved then there will be some degree of undesirable deposition of liquid particles in the endotracheal tube and shallow pulmonary passageways. In this context, it is desirable in many cases to administer drugs in a liquid phase rather than a gaseous phase, to obtain proper absorptive and/or therapeutic effects. Therefore, in many circumstances, the Malzoomdoost device may not avoid important drawbacks present in other coupled external nebulizing devices. In addition to these drawbacks, the high pressure gas injection mechanism of Mazloomdoost is specifically designed for use in conjunction with the HFJV type of ventilation system, which is a specialized ventilation system of limited clinical utility compared to conventional NVC ventilation.

In view of the above, it is not surprising that coupled external nebulizing devices have received limited acceptance in the medical community. Illustrative of this fact, the American Heart Association's (AHA) current guidelines for standard intrapulmonary drug administration (STD) for emergency cardiac care do not embrace the use of coupled external nebulizing devices. Instead, the 1994 AHA recommendations for STD call for the following procedure. A long, through-the-needle intracatheter is threaded down the inside of the endotracheal tube. CPR compressions must then be interrupted while two to two and a half times the normal dose of medication is forcefully injected through the catheter, followed by a 10 ml flush of saline. In the event that an intracatheter is unavailable, the medication may be delivered using a heparin lock with a 20 gauge needle through the wall of the endotracheal tube to deliver medication in a forced spray form at the distal tip of the endotracheal tube. The AHA recommended procedure for STD exhibits most of the disadvantages of coupled external nebulizing devices, however it is technically simpler, less expensive and more readily available in emergency settings.

In view of these disadvantages of coupled external nebulizing devices and STD methods, further attempts to develop effective intrapulmonary drug administration technology have been undertaken. A number of devices have been developed which use a narrow intracatheter to bypass the endotracheal lumen, limiting the surface area for drug deposition between the external (proximal) section of the intracatheter and the internal (distal) tip of the catheter. These devices also parallel the STD method in that they rely, at least in part, on a forceful plunging action of a syringe to produce a jet-like spray of medication at the distal tip of the intracatheter, for deeper delivery. However, unlike the STD technology, each of the subject devices incorporate the intracatheter directly within the lumen or wall of the endotracheal tube, or provide an intracatheter which is otherwise conveniently insertable into the endotracheal tube. Examples of such devices include the Emergency Medication Tube (EMT™) (Mallinkrodt Medical, Inc., St. Louis, Mo.), the ENDO-JEC™ (Autovage®, Library, Pa.), and the devices described in U.S. Pat. No. 5,031,613 issued to Smith et al. on Jul. 16, 1991, and U.S. Pat. No. 4,955,375, issued to Martinez on Sep. 11, 1990.

Certain of the above, intracatheter devices add one or more additional features over the STD technology. The most important of these added features is a narrow-valved nozzle or, alternatively, an impact barrier, at or near the distal tip of the intracatheter. The function of this valve or barrier is to disperse the medication stream at the distal tip, to provide deeper delivery of the medication into the pulmonary passageways. Thus, U.S. Pat. No. 5,031,613 to Smith describes an hourglass-shaped valve and perforated wall at the distal tip of the intracatheter, designed to accelerate and disperse the medication stream in the manner of a garden nozzle. Another example of a terminal valved intracatheter design is shown in U.S. Pat. No. 4,995,375 to Martinez. Martinez provides an intracatheter associated with the wall of the endotracheal tube, which has a flared distal nozzle anchored to the wall of the endotracheal tube. The flared, anchored nozzle is intended to disperse liquid medications forcefully injected into the intracatheter. In addition, the intracatheter wall of the Martinez device is elastic and is normally in a deflated condition. When the medication is injected into the intracatheter, the wall reportedly deforms and then exerts elastic force to help expel the medication stream forcefully from the distal tip. In an alternative dispersal design, the Mallinkrodt EMT™ uses an oval shaped window in the distal wall of standard endotracheal tubes (the Murphy eye; designed to ensure patency of the tube) as an impact barrier to disperse the medication stream near the intracatheter tip. The intracatheter is secured to the wall of the endotracheal tube and its distal aperture is directed at the edge of the Murphy Eye. When the medication is forcefully injected into the proximal end of the intracatheter, it exits as a stream and impinges on the Murphy eye edge, reportedly causing dispersal of the medication stream.

As with the other prior art devices discussed above, the valve or barrier-equipped intracatheter/endotracheal tube devices are also limited in their ability to provide effective intrapulmonary drug delivery. The terminal valve and barrier designs do not achieve a true aerosolizing effect, so the flow of medication produced at the distal tip is a stream or at best a spray of large liquid droplets. These droplets are only weakly propelled by the positive airflow of NVC ventilation. Consequently, the medication is not delivered uniformly to the deep, absorptive pulmonary tissues, but is largely delivered in irregularly distributed droplets deposited within the shallow pulmonary passages.

Significant medical problems attend the use of all of the above mentioned intrapulmonary drug delivery devices and methods, which problems relate to the inability of these devices to deliver a uniform spray of fine particulate liquid medication to the deep pulmonary tissues. Because of this drawback, it is difficult to provide a therapeutic dose of medication. More commonly an excessive dose must be provided, because the medication coats the shallow pulmonary passageways where absorption into the pulmonary circulation is slow and unpredictable. This results in drug pooling, or a prolongation of the active period of the medication. Drug pooling can be profoundly deleterious in many cases. For example, in post-resuscitated cardiac patients pooling of resuscitative drugs can cause increased cardiac afterload and myocardial oxygen consumption. In addition to the pooling problem, the requirement for excessive doses of medication a therapeutic dose can cause increased airway pressures and resistance, which may interfere with patient ventilation efforts.

In view of the above, an important need exists in the medical arts for drug delivery devices which can improve the accessibility, quality and cost of emergency medical care. In particular, there is a need for drug delivery devices which can provide rapid and effective administration of life saving medications to emergency patients in situations where intravenous access is unavailable or problematic.

Because of the known potential advantages of intrapulmonary drug delivery, and in view of the poor efficacy of prior art devices for this purpose, there is a further need in the medical arts for an intrapulmonary drug administration device that can provide a uniform, accurate, therapeutic dose of medication deep within the pulmonary passageways. A related need exists for such an effective intrapulmonary drug delivery device which can be used for a variety of purposes in a variety of settings, in conjunction with standard emergency and clinical equipment and procedures.

SUMMARY OF THE INVENTION

It is therefore an object of the present invention to provide an intrapulmonary drug administration device that will administer a uniform, accurate, therapeutic dose of medication to the deep pulmonary tissues. It is a further object of the invention to achieve the above object in a device which is adaptable to a variety of purposes in a variety of settings, and which can be used in conjunction with standard emergency and clinical equipment and procedures.

The invention achieves these objects and other objects and advantages by providing an endotracheal catheter assembly adapted for intrapulmonary transfer of liquid therapeutic agents deep within the pulmonary passageways of mammalian patients. The catheter assembly includes a first, gas-bearing tube with an outer and inner wall, a lumen, a proximal section and a distal tip. The gas-bearing tube has an anatomically determined length to allow the tube to be inserted in an airway of the patient to position the distal tip near a carina of the patient. The catheter assembly also includes a second, liquid-bearing tube about the same length as the first tube which also has outer and inner walls, a lumen, a proximal section and a distal tip. The first tube has a gas-receiving port to allow transfer of gas to and from the lumen of the first tube, and the second tube has a liquid-receiving port to allow transfer of liquid to and from its lumen. The distal tips of the first and second tubes are arranged to form a nozzle, at which part of the catheter assembly the lumen of the first tube has a comparative cross-sectional area relative to that of the second tube's lumen of between about 0.4:1.0 and 4.0:1.0. In addition to these relative cross-sectional areas of the tubes, preferred embodiments of the invention call for inner diameters of the tubes to be within a specified range; between about 0.018 cm and 0.480 cm for the first tube, and between about 0.016 cm and 0.184 cm for the second tube.

In preferred embodiments of the invention, the second tube is nested within the lumen of the first tube between the proximal section and distal tip of the first tube. This configuration permits gas to pass unobstructed between the inner wall of the first tube and the outer wall of the second tube, which results in a high velocity gas/liquid interface being formed at the nozzle when high velocity gas is forced from the first distal tip and liquid is expelled from the second distal tip.

In alternate embodiments of the invention, the first and second tubes form part of a single, bi-lumenal catheter. In this design, the first and second tubes are separated by a longitudinal septum which divides the catheter, separating the gas-bearing and liquid-bearing lumens. Accordingly, the high velocity gas/liquid interface is not circumferential around the distal tip of the second tube, but forms instead as a roughly linear interface adjacent the septum.

In preferred embodiments of the invention, the catheter assembly has a coupling device to couple the assembly to a standard, ventilatory endotracheal tube. The coupling device is designed to enable the first and second tubes to be sealably inserted into a lumen of the endotracheal tube. In related embodiments, a standard, ventilatory endotracheal tube is coupled by such a coupling device to the catheter assembly, optionally by a standard ventilator connector which is modified to sealably receive the first and second tubes of the assembly.

In yet other preferred embodiments, the catheter assembly is coupled to an endotracheal tube, and the first and second tubes of the catheter assembly can be selectably, lockably repositioned longitudinally within the lumen of the endotracheal tube. This allows the nozzle of the catheter assembly to be selectably lockably repositioned relative to a distal tip of the endotracheal tube.

In other embodiments of the invention, the catheter assembly is provided with an axial orientation marker visible on the assembly when the nozzle of the assembly is endotracheally inserted and, in addition, the nozzle is split or otherwise adapted to form two bilateral hemi-nozzles. By visualizing the marker and axially manipulating the catheter assembly, a health care worker can orient the nozzle so that each of the hemi-nozzles point toward one of the patient's lungs when the nozzle is positioned near the carina. In related embodiments, the catheter assembly has a longitudinal orientation marker visible when said the nozzle is partially endotracheally inserted, so that the nozzle can be longitudinally positioned adjacent to the carina.

In yet other preferred embodiments of the invention, the catheter assembly is designed so that the second tube is removably nested within the lumen of the first tube, so that the second tube can be removed from the first tube. This allows the lumen of the first tube to be enlarged to adapt the first tube for multi-purpose use.

In a more detailed embodiment of the invention, the catheter assembly includes a first, gas-bearing tube with an outer and inner wall, a lumen, a proximal section and a distal tip. This gas-bearing tube also has a suitable length to insert the tube in a patient's airway to position the distal tip near the carina. This embodiment includes a second, liquid-bearing tube about the same length as the first tube, which also has outer and inner walls, a lumen, a proximal section and a distal tip. However, unlike the previously described embodiments of the invention, the present embodiment also has a third tube of about the same length as the first and second tubes. The third tube also has inner and outer walls, a lumen, a proximal section and a distal tip. The first and third tubes both have gas-receiving ports to allow transfer of gas to and from their lumens, and the second tube has a liquid-receiving port to allow transfer of liquid to and from its lumen. The distal tips of the first, second and third tubes are arranged to form a nozzle. At the nozzle, the lumens of the first and third tubes have a combined cross-sectional area relative to the cross-sectional area of second tube's lumen of between about 0.4:1.0 and 4.0:1.0. In addition to these relative cross-sectional areas of the tubes' lumens, preferred embodiments of the invention also call for the inner diameter of the first tube to be no greater than 0.5 cm.

In tri-lumenal embodiments of the invention, it is preferable to have the second tube is nested within the lumen of the first tube, and the third tube nested within the lumen of the second tube. In this design, gas can pass unobstructed at the nozzle between the inner wall of the first tube and the outer wall of the second tube, as well as within the third lumen. This provides for a multi-front, circumferential high velocity gas/liquid/high velocity gas interface to form when high velocity gas exits the first and third distal tips and liquid exits the second distal tip.

In alternate, tri-lumenal embodiments of the invention, the three tubes are not separate, but are integrated within a single, tri-lumenal catheter. In these embodiments, the first, second and third tubes are separated by septae which longitudinally divide the catheter into three separate lumens.

In addition to the above described devices, the invention also provides methods for using the devices for intrapulmonarily administering liquid therapeutic agents to mammalian patients. The methods involve inserting a multi-lumen catheter assembly which has a high velocity gas-bearing lumen and a separate, liquid-bearing lumen into the trachea to position a nozzle of the catheter assembly near the carina. Then a flow of high velocity gas is forced through the gas-bearing lumen toward the nozzle to exit the nozzle near the carina. To complete the method, a liquid therapeutic agent is introduced into the liquid bearing lumen and, while gas is exiting the nozzle, the liquid therapeutic agent is expelled from the nozzle at an high velocity gas/liquid interface. This results in the liquid therapeutic agent being deformed into a fine particulate aerosol by the gas, which propels the liquid deep within a pulmonary passageway of the patient.

In preferred methods of the invention, the liquid therapeutic agent is a liquid drug, and the expulsion of the drug from the nozzle delivers a plasma concentration of the drug into the bloodstream of the patient which is approximately equivalent to a plasma concentration of the drug which can be measured after a similar amount of the drug is administered to the patient intravenously. In yet more preferred methods, the expulsion of the liquid drug from the nozzle delivers a dose of the drug which is at least approximately bioequivalent to an intravenously delivered dose of a similar amount of the drug.

Other methods of the invention are provided which include coupling the cathether system to an endotracheal tube and a ventilator system. In preferred embodiments of these methods, Normal Volume Cycled ventilation (NVC) is delivered to the patient via the endotracheal tube and Continuous Positive Airway Pressure (CPAP) ventilation is delivered as high velocity gas flow through the gas-bearing lumen, resulting in a constructive ventilatory effect, which increases the functional residual capacity of the patient's lungs. Accordingly, this method results in enhanced delivery, absorption and diffusion of the liquid therapeutic agent.

Yet other preferred methods of the invention include the step of removing a liquid-bearing tube nested within the gas-bearing lumen from the gas-bearing lumen after the liquid therapeutic agent is expelled from the nozzle. After the liquid-bearing tube is removed, the gas bearing tube can then be used for a variety of other purposes, such as coupling a pressure transducer to the gas bearing lumen to detect patient inspiratory effort for assist control (AC) ventilation, application of suction to remove fluids and or cells for biopsy purposes from the patient's airway, and other uses.

BRIEF DESCRIPTION OF THE DRAWINGS

FIG. 6 is a partial sectional view showing distal tips of inner and outer tubes which make up the nozzle of the catheter assembly.

FIG. 7 is a sectional view of an alternate, tri-lumenal catheter having an alternate nozzle configuration.

FIG. 8 is a cross sectional view of a bi-lumenal catheter assembly, having gas-bearing and liquid-bearing tubes separated by a longitudinal septum.

FIG. 9 is a cross sectional view of a tri-lumenal catheter assembly, having two gas-bearing tubes and one liquid-bearing tube separated by longitudinal septae.

FIG. 10 is a cross sectional view of a tri-lumenal catheter assembly, having two, semi-lunar gas-bearing tubes surrounding a central, liquid bearing tube.

FIG. 11 is an isometric view depicting an alternate nozzle configuration of the invention having distal tips of the inner and outer tubes branched to form a nozzle with two, bilateral hemi-nozzles.

FIG. 12 is an isometric view depicting an alternate nozzle configuration having distal tips of the inner and outer tubes branched compressed to form a nozzle which is bi-concave in cross section so as to form two, bilateral hemi-nozzles.

FIG. 13 is an isometric view of an alternate embodiment of the invention having an inflatable balloon cuff surrounding the distal tip of the gas-bearing tube.

FIG. 14 is a graph showing how plasma concentration of a selected drug changes as a function of time after administration of the drug using prior art devices, versus the invention.

DETAILED DESCRIPTION OF THE INVENTION

Figure 1:
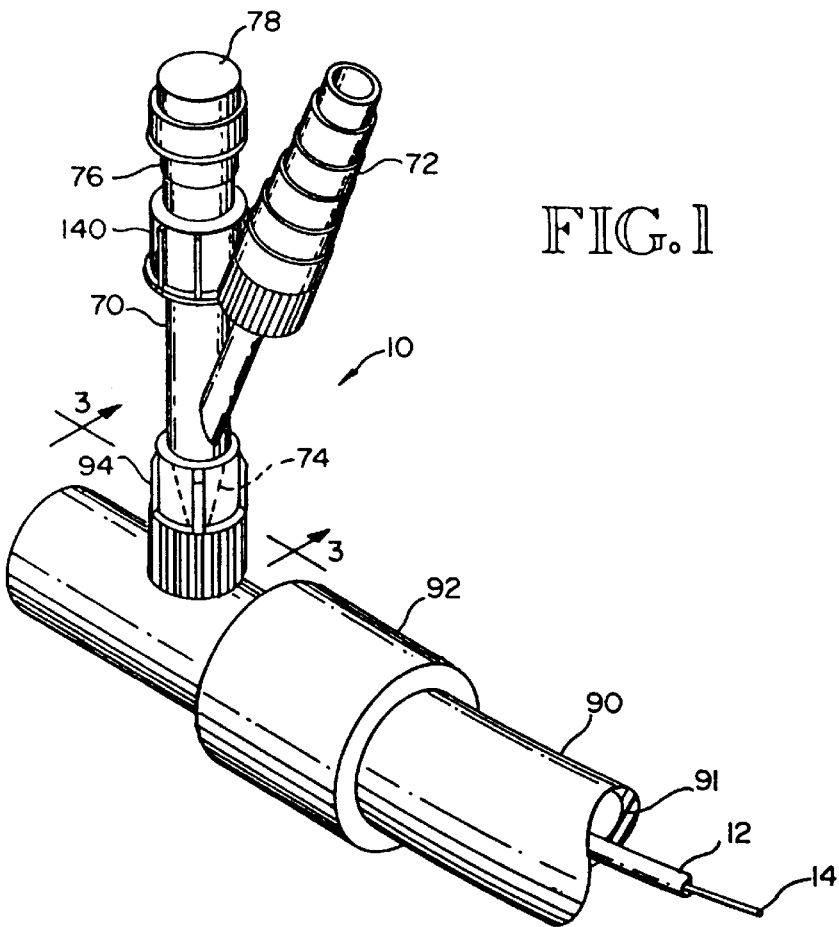
FIG. 1 is an isometric, cut away view of a portion of an endotracheal catheter assembly employing the concepts of the present invention, showing the catheter assembly connected to a partial endotracheal tube via a standard ventilator connector.

The invention provides a novel endotracheal catheter assembly adapted for efficient, uniform intrapulmonary transfer of liquid therapeutic agents deep within the pulmonary passageways of mammalian patients. A catheter assembly 10 employing the concepts of the invention is depicted in FIGS. 1–13. Referring to FIG. 1, the assembly includes a first tube 12 which is a gas-bearing tube, and a second tube 14 which is a liquid-bearing tube. Referring to FIGS. 3 and 6, the first tube has a first outer wall 16, and a first inner wall 18 defining a first lumen 20. The second tube has a second outer wall 22, and a second inner wall 24 defining a second lumen 26.

Figure 2:
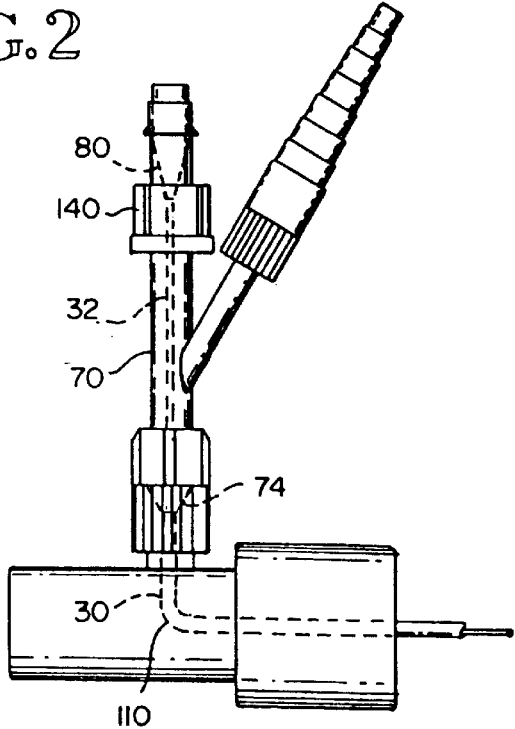
FIG. 2 is an isometric view of a portion of the catheter assembly of the invention, showing the oxygen and medication ports, and depicting the proximal sections of the first and second tubes in phantom.
Figure 3:
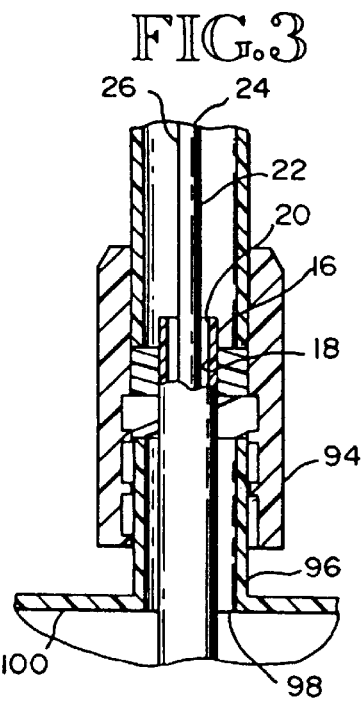
FIG. 3 is a sectional view, taken along lines 3—3 of FIG. 1, of a portion of the catheter assembly showing an adapter and port for connecting the catheter assembly to an endotracheal tube via a standard ventilator connector.

Referring to FIG. 2, the first tube 12 has a first proximal end 30, and the second tube 14 has a second proximal end 32. The first proximal end and second proximal end are connected to liquid or gas receiving structures which allow transfer of gas to and from the first lumen 20, and transfer of liquid to and from the second lumen 26. These liquid and gas receiving structures preferably serve to connect the first lumen to a gas source (not shown), such as an ambu bag or conventional low pressure ventilator for providing air or oxygen to patients in emergency or hospital care situations, and the second lumen 22 to a liquid source (not shown), preferably a liquid carrying syringe.

Referring to FIGS. 6 and 7, the first tube 12 of the catheter assembly has a first distal tip 40 at an opposite end of the tube from the first proximal section 30. The second tube 14 has a second distal tip 42 at an opposite end of the tube from the second proximal 32. Collectively, the first and second distal tips define a nozzle 44 at which gas from the first tube and liquid from the second tube can be expelled. The first and second tubes are of approximately similar lengths, suitable for inserting the tubes into an airway of the patient so as to position the nozzle in the trachea near a carina of the patient. Accordingly, the tubes will generally be between 10–46 cm, preferably between 15–41 cm, and more preferably between about 20–38 cm, depending on the airway anatomy of the intended patient. Tube length will preferably be determined on the basis of average human anatomy, but in the event that the present invention is used on other species, the parameters can easily be modified to facilitate special treatment facilities or methods.

In preferred embodiments of the invention, the second tube 14 is nested within the first lumen 20 between the first proximal section 30 and first distal tip 40. This configuration permits gas to pass unobstructed between the first inner wall 24 and the second outer wall 22. This configuration is particularly beneficial because the invention relies on high velocity gas flow exiting the first lumen at the first distal tip to aerosolize liquid expelled from the second distal tip 42 at a high velocity gas/liquid interface formed between the first and second distal tips at the nozzle 44. In particular, the nested configuration of the second tube within the first tube which results in a high velocity gas/liquid interface is circumferential relative to the second distal tip, and which therefore maximizes the area of the interface to facilitate aerosolization of the liquid by the high velocity gas flow.

Effective aerosolization of liquid expelled from the first lumen 20 at the nozzle 44 depends in large part on the relative cross-sectional areas of the first lumen and second lumen 20. As an initial point, high velocity gas flow from the first distal tip 40 is required at the nozzle in order to effectively deform the liquid into an aerosol. Velocity of gas flow is a function of the cross-sectional surface area of the first lumen and the initial velocity of gas flow entering the first proximal section 30 from the gas supply. The invention preferably uses a standard ventilator gas supply connected to the proximal section by standard oxygen supply tubing (4.0 mm diameter), which typically delivers a constant, low velocity flow of 10.0 liters per minute. However, because high velocity gas flow from the first distal tip is desired, the cross sectional area of the first lumen, at least at the location of the first distal tip, is preferably significantly lower than a cross sectional area of the gas supply tubing lumen. For the purpose of delivering a high velocity gas flow at the nozzle, a satisfactory first inner diameter 50 (see FIG. 7) of the first tube is between about 0.18 cm and 0.480 cm. More preferably, the first tube inner diameter is between about 0.027 cm and 0.240 cm, and most preferably between about 0.114 and 0.122 cm. By thus gauging down the gas flow pathway, the velocity of gas flow delivered at the nozzle is dramatically increased. For example, if a selected first inner diameter is about 0.043 cm, and the first lumen is otherwise unoccupied, the cross-sectional surface area of the gas flow pathway is decreased by a factor of about 86. The resulting velocity increase of the gas flow is about 19.5 times. The velocity increase is not directly proportional to the cross-sectional area decrease, because the extreme cross-sectional area decrease used in the invention cause compression of the gas and increase in the density of the gas. Nonetheless, with a gauge down to a 0.043 first inner diameter, gas flow velocity is increased from about 8.5 meters per second to about 166 meters per second.

When the high velocity gas flow exiting the first distal tip 40 at the nozzle 44 interfaces with a liquid expelled from the second distal tip 42 at the high velocity gas/liquid interface, slight negative pressure tends to draw liquid from the second lumen 26 toward the nozzle. However, much more than negative pressure is used in the invention to aerosolize the liquid. To particulate the liquid into an aerosol, work must be done. The work is best describe in terms of translational kinetic energy (KE). KE in this system is proportional to the mass of a particle of the liquid, and is also proportional to the square of the velocity of the gas impinging on the liquid. Accordingly, if the velocity of the gas is doubled, the KE is increased by four times, so that four times the work is available to aerosolize the liquid. In the model presented above, where gauging down of the first inner diameter 50 to 0.043 cm yields a 19.5 fold velocity increase, the resulting increase in KE available to deform the liquid into an aerosol is nearly 400 fold.

The relative cross sectional area ratio between the first lumen 20 and the second lumen 26 is a critical aspect of the invention for achieving "true constant high velocity" gas flow at the nozzle 44. In one embodiment of the catheter assembly 10, the first lumen has a comparative cross-sectional area relative to that of the second lumen, at the position of the nozzle, of between about 0.4:1.0 and 4.0:1.0. More preferably, the cross-sectional area of the first lumen relative to the cross-sectional area of the second lumen at the nozzle is between approximately 1.0:0.6 and 2.0:1.0, and most preferably between about 0.9:1.0 and 1.0:1.0.

A suitable second inner diameter 52 of the second tube 14 to provide the desired relative cross-sectional areas of the tube lumens has been found to be within the range of about 0.016 cm to 0.184 cm (when the first inner diameter is between about 0.018 cm to 0.480). Preferably, the second inner diameter is in the range of between about 0.024 cm and 0.090 cm (corresponding to a first inner diameter of between about 0.027 cm and 0.240 cm), and more preferably between about 0.040 cm and 0.048 cm (corresponding to a first inner diameter of between about 0.114 cm and 0.122 cm). Optimal tube inner diameters to yield a desired inner:outer lumen cross-sectional area ration will also depend upon wall thicknesses of selected tubing stocks.

Although it is preferred to use a catheter assembly 10 with the second tube 14 nested within the first lumen 20, alternate embodiments of the invention are provided wherein the first and second tubes form part of a single, bi-lumenal catheter, as shown in FIG. 8. In this design, the first and second tubes are separated by a longitudinal septum 60 which runs between the proximal ends 30, 32 and the distal tips 40, 42 and divides the cathether, separating the gas-bearing first lumen and liquid-bearing second lumen. In this embodiment, the high velocity gas/liquid interface at the nozzle is not circumferential around the distal tip of the second tube, but forms instead as a roughly linear interface adjacent the septum.

Figure 4:
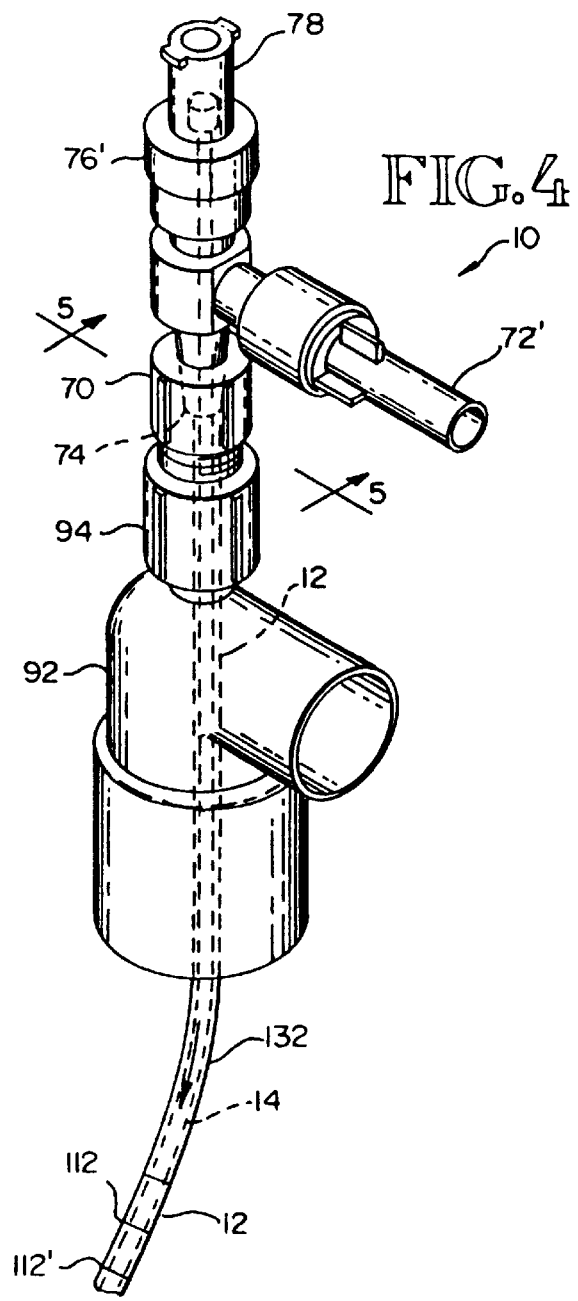
FIG. 4 is an isometric view depicting an alternate embodiment of the catheter assembly featuring an alternate adapter, medication port, and ventilator connector configuration.

With regard to the liquid and gas receiving structures connected to the first proximal end 30 and second proximal end 32, these structures for coupling the catheter assembly 10 to a gas and liquid supply can be selected from a wide variety of suitable port and connector designs. Referring to FIG. 1, a preferred embodiment of the invention includes a standard Y-adapter 70 conventionally used for intravenous drug administration, modified for gaseous connection of a gas source (not shown) to the first lumen 20, and liquid connection of a liquid source (not shown) to the second lumen 26. In this embodiment the Y-adapter includes an oxygen port 72 for connection to a standard, 4 mm diameter oxygen tubing. The oxygen port is gaseously connected to the first lumen which is sealedly joined to the Y-adapter at a base 74 of the adapter. Also in this embodiment, the Y-adapter includes a luer-locking medication injection port 76 with a silicone injection diaphragm for receipt of liquids, for example liquid drugs, from a syringe needle. The medication port is liquidly connected to the second lumen which is sealedly joined to a base 80 of the medication port (see FIG. 2). Alternative designs of the oxygen and medication ports are depicted in FIG. 4. Instead of a Y-adapter, a T-shaped adapter 70' is provided. Also, an alternative oxygen port 72' with a smooth-bored tubing mount can be used, as well as a more sophisticated, medication port with a needleless syringe receptacle having a one way check valve to prevent medication reflux after medication delivery into the port and second lumen.

In preferred embodiments of the invention, the catheter assembly 10 has a coupling mechanism to couple the assembly to a standard, ventilatory endotracheal tube 90, as depicted in FIG. 1. In related embodiments, the endotracheal tube is already coupled by such a coupling device to the catheter assembly. Endotracheal tubes are largely uniform in their construction, and are routinely used to intubate patients in both emergency and hospital care environments to provide a conduit for ventilating the patient, typically by normal volume cycled (NVC) ventilation. In this application, the endotracheal tube is generally inserted into the patient's airway so that a distal tip (not shown) of the endotracheal tube is at about the level of the carina. Then the endotracheal tube is connected to a ventilation source and air or oxygen is delivered to the patient's lungs via a lumen 91 of the endotracheal tube. For coupling the catheter of the invention to the endotracheal tube, it is preferable, to use a standard, 15–22 mm ventilator connector 92, which is modified to sealably receive the first and second tubes 12, 14 of the catheter assembly and to provide a passageway to insert the nozzle 44 of the assembly into the lumen of the endotracheal tube. Briefly, the ventilator connector can be modified for example to include a sealable catheter port, such as a connector luer lock 94 mated to a male coupling 96 which defines an aperture 98 in a wall 100 of the ventilator connector, as depicted in FIGS. 1 and 3. The ventilator connector can be a straight connector, as shown in FIG. 1, or, more preferably an elbow-shaped connector, as shown in FIG. 4, which minimizes formation of bends 100 (see FIG. 2) in the first and second catheter tubes.

Figure 5:
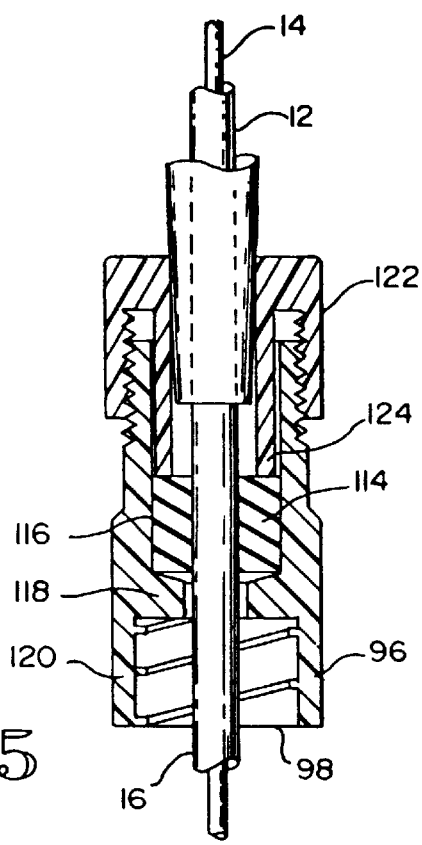
FIG. 5 is a sectional view, taken along lines 5—5 of FIG. 4, showing details of the alternate adapter, including a compression sleeve for lockably adjusting a position of a nozzle of the catheter assembly relative to a distal tip of an endotracheal tube.

To couple the catheter assembly 10 to the endotracheal tube 90, the nozzle is preferably threaded through the aperture 98 of the ventilator connector 92 and into the endotracheal tube lumen 91. Preferably, the catheter assembly is provided with longitudinal orientation markers, such as centimeter incremental lines 112, 112' on the first tube 12 when the nozzle is partially endotracheally inserted, so that the nozzle can be longitudinally positioned adjacent to the carina. These markers can be used to position the nozzle near the carina when the device is used separate from an endotracheal tube, or can be used to position the nozzle in a desired location near the distal tip of the endotracheal tube when coupled therewith, by aligning the markers with comparable markers provided on the endotracheal tube. Once the desired positioning of the nozzle near the carina has been achieved, it is also preferable to secure the nozzle in this position. Accordingly, the first and second tubes of the catheter assembly can be selectably, lockably repositioned longitudinally within the lumen of the endotracheal tube to allow the nozzle to be selectably lockably repositioned relative to a distal tip of the endotracheal tube. One suitable design to accomplish this function is depicted in FIG. 5. The male coupling 96 on the ventilator connector 92 (not shown in the figure) can be provided with a selectable locking mechanism as follows. Where the first and second tubes 12, 14 pass through the male coupling (after the nozzle 44 has been threaded through the male coupling and aperture 98 of the ventilator connector into the endotracheal tube lumen), the male connector is provided with a compressible sleeve 114, preferably made of soft silicon material. The sleeve surrounds the first tube and laterally abuts an inner wall 116 of the male coupling, and is held in place by a retainer 118 near a base 120 of the male coupling. The male coupling is provided with a cap 122 which has a cap lower portion 124 which inserts into the male connector and can be made to compress the sleeve therein against the retainer (for example by providing the cap and male coupling with mated threads so the cap can be threaded downward toward the sleeve). When the sleeve is thus compressed against the retainer, it is forced outward against the inner wall of the male coupling, and also against the first outer wall 16 if the first tube, thereby selectably locking the inner tube against longitudinal repositioning. This in turn secures the nozzle in place after it has been longitudinally positioned to be located near the carina.

Another preferred aspect of the invention is a modified nozzle 44 which is bifurcated or otherwise adapted (eg. by forming or medially compressing the tubes into a bi-concave, cross-sectional shape) to form two bilateral hemi-nozzles 130, 130' (see FIGS. 11 and 12). In this embodiment, an axial orientation marker, such as the arrow 132 on the first tube 12 shown in FIG. 4, is also provided which is visible when the nozzle is inserted to the level of the carina. By visualizing the axial marker and axially manipulating the catheter assembly, a health care worker can orient the nozzle so that each of the hemi-nozzles point toward one of the patient's lungs when the nozzle is positioned near the carina.

In yet other preferred embodiments of the invention, the catheter assembly is designed so that the second tube 14 is removably nested within the first lumen 20, so that the second tube can be removed from the first tube. As shown in FIGS. 1 and 2, this can readily be accomplished by providing the medication port 76 with a luer locking cap 140 which includes the base 80 of the medication port (see FIG. 2), to which the second tube is sealedly connected. With this design, the second tube can be readily removed from the first lumen by unlocking the cap and pulling the cap and first tube away from the remainder of the catheter assembly. This allows the lumen of the first tube to be enlarged to adapt the first tube for multi-purpose uses. Examples of such multi-purpose uses include monitoring of expiratory $CO_2$ (by intermittently or continuously sucking expired gases through the first tube from near the carina using a commercial $CO_2$ sampling device), and pressure monitoring for assist control (AC) ventilation. In the latter application, the first tube is connected to a pressure transducer of an assist controlled ventilator (eg. by connecting the transducer to the oxygen or medication ports). The transducer senses ventilator effort of the patient and controls timing of ventilation from to coincide with the patient's endogenous breathing cycle, thereby minimizing ventilatory effort of the patient.

In a more detailed embodiment of the invention, the catheter assembly includes the first, gas-bearing tube 12 and second, liquid-bearing tube 14, as described above. However, unlike the previously described embodiments of the invention, this alternate embodiment includes a third tube 150 (see FIGS. 7, 9 and 10) of about the same anatomical length as the first and second tubes. The third tube has a third outer wall 152, a third inner wall 154, and a third lumen 156. Likewise it has a third proximal section (not shown, but co-terminal with the first proximal section 30) and a third distal tip 158. The first and third tubes both connectable to a gas supply by similar gas-receiving structures as described above. Likewise, the second tube is connectable to a liquid supply by similar liquid-receiving structures as described above. Also in this embodiment, the first, second and third distal tips 40, 42, 158 are arranged to form a nozzle 44. At the nozzle, the first lumen 20 and third lumen 156 preferably have a combined cross-sectional area relative to the cross-sectional area of the second lumen 26, at the position of the nozzle, of between about 0.4:1.0 and 4.0:1.0. Preferably, the combined cross-sectional area of the first and third lumens relative to that of the second lumen at the nozzle is between approximately 1.0:0.6 and 2.0:1.0, more preferably between approximately 0.9:1.0 and 1.0:1.0. In addition to these relative cross-sectional areas of the tubes, preferred embodiments of the invention feature an inner diameter of the first tube to be no greater than 0.5 cm.

In tri-lumenal embodiments of the invention (FIGS. 7, 9 and 10), it is also preferred to have the second tube nested 14 within the first lumen 20, and the third tube 150 nested within the second lumen 26 (as shown in FIG. 7). In this design, gas passes unobstructed at the nozzle 44 between the first inner wall and the second outer wall 22, as well as within the third lumen 156. This increases the circumferential high velocity gas/liquid/high velocity gas interface that forms when the catheter assembly is in use for liquid delivery, because high velocity gas exiting the first and third distal tips, 40, 158 impacts the liquid exiting the second distal tip 42 at two opposing fronts.

In alternate, tri-lumenal embodiments of the invention, the three tubes are not separate, but are integrated within a single, tri-lumenal catheter. In these embodiments, the first, second and third tubes can be separated by septae 60', 60" (FIG. 9) which longitudinally divide the catheter into three separate lumens. Alternatively, the embodiment shown in FIG. 10 has two, semi-lunar gas bearing lumens 20, 156 surrounding a central, liquid bearing lumen 20.

A further aspect of the invention is that performance of the catheter assembly 10 can be altered by altering relative positioning of the first distal tip 40, second distal tip 42, and/or third distal tip 158 to change configuration of the nozzle 44. When determining the relationship of the distal tips to one another, the second distal tip is preferably recessed slightly within the first distal tip, for maximum aerosolization, directionality and spray distance. A recession of 0.5–3 mm is preferred. Furthermore, if a third tube is used within the second tube, the third distal tip preferably is recessed in second distal tip, at approximately the same distance as the second tip is recessed in the first distal tip. Use of a third tube will result in a more narrow field of spray than use of two tubes. Moreover, this configuration allows for even greater circumferential shear force application to the inner medication conduit. By recessing the third lumen at different lengths, the directionality of the aerosolized medication spray can be also be changed, because the vector addition of applicable force components change, whereby directionality of aerosolized particles driven by the gas flow can be optimized.

Method of Use

In addition to the above described devices, the invention also provides methods for using the devices for intrapulmonarily administering liquid therapeutic agents to mammalian patients. The methods involve inserting the multi-lumen catheter assembly 10 described above to into the trachea to position the nozzle 44 near the carina. Then a flow of high velocity gas is forced through the first lumen 20 toward the nozzle to exit the nozzle near the carina. To complete the method, a liquid therapeutic agent is introduced into the second lumen 26 and, while gas is exiting the nozzle, the liquid therapeutic agent is expelled from the second distal tip 42 at a high velocity gas/liquid interface. This results in the liquid therapeutic agent being deformed into a fine particulate aerosol by the gas, which propels the liquid deep within a pulmonary passageway of the patient.

In preferred methods of the invention, the liquid therapeutic agent is a liquid drug, and the expulsion of the drug from the nozzle delivers a plasma concentration of the drug into the bloodstream of the patient which is approximately equivalent to a plasma concentration of the drug which can be measured after a similar amount of the drug is administered to the patient intravenously. Determination of equivalent plasma concentrations of similar doses of drugs delivered intravenously and intrapulmonarily via the invention can be done by routine monitoring techniques which measure plasma drug concentrations at specific times after the dose is delivered. In yet more preferred methods, the expulsion of the liquid drug from the nozzle delivers a dose of the drug which is at least approximately bioequivalent to an intravenously delivered dose of a similar amount of the drug. Bioequivalency studies are also routine in the art, and they generally depend on measurements of an expected physiological response after administration of a specific drug. If comparable (eg. within about a 25% range of measured values) physiological responses are observed after a similar amount of a selected drug is delivered intravenously, versus intrapulmonarily using the invention, then the dose delivered using the invention is "at least substantially bioequivalent" within the meaning of this description. Preferably, bioequivalency is even closer, as evidenced by close, comparative correlations of plasma concentration changes over time with a temporal profile of physiological response changes over time, between the two methods, as exemplified in the examples below.

Other methods of the invention are provided which include coupling the cathether system 10 to an endotracheal tube 90 and a ventilator system (not shown). In preferred embodiments of these methods, Normal Volume Cycled ventilation (NVC) is delivered to the patient via the endotracheal tube, and Continuous Positive Airway Pressure (CPAP) ventilation is delivered as high velocity gas flow through the first lumen 20 and/or third lumen 156, resulting in a constructive ventiatory effect. This overlapping ventilation method increases the functional residual capacity of the patient's lungs and thereby results in enhanced delivery, absorption and diffusion of the liquid therapeutic agent.

Yet other preferred methods of the invention include the step of removing the second tube 14 from a nested position within the first lumen after the liquid therapeutic agent is expelled from the nozzle 44. After the second tube is removed, the first tube can then be used for a variety of alternative purposes, as described above.

The catheter assembly 10 of the invention is not limited to use in conjunction with an endotracheal tube. Rather, the assembly can be used alone for a variety of purpose, including local anesthetic delivery and lavage/suction biopsy as is often performed in AIDS patients. When the catheter assembly is used alone, it is preferable to provide an inflatable cuff 160, preferably made of latex, which can be inflated from gas exiting terminal holes 162 in the first outer wall 16 of the first tube 14. This prevents the nozzle 44 from flailing against sensitive tissues in the patients airway when high velocity gas flows therethrough.

Patients who would receive benefit from the present invention include those who are in cardiac arrest, premature infants who require pulmonary surfactant, comatose HIV patients who may benefit from direct administration of petamidine for pneumocystis carinii infection, and comatose or chronically ventilator-dependent patients in whom intravenous administration is not capable of being carried out in practice.

An ancillary benefit of the invention is that it can be used to deliver oxygen to patient's during intubation. It is not normally possible to deliver oxygen through a standard endotracheal tube during an intubation process unless an unwieldy resuscitation bag or inflexible ventilator tube is connected to the tube, making maneuvering of the tube during intubation difficult. With the catheter assembly coupled to the endotracheal tube, only the small, flexible oxygen tubing need be connected to deliver oxygen to the patient during intubation.

The materials by which the present invention may be made include any medically suitable materials. For instance, stainless steel and the entire group of plastics, thermosetting plastics and thermoplastics, including both amorphous and crystalline plastics may be used. Flexibility of the material is preferred, but not a necessary element of the present invention. Preferably, the material is inexpensive enough that it is disposable after use. The most preferred tube material for performance and cost purposes is a polyurethane. However, the catheter assembly can also be coupled with a high pressure oxygen system, in which case a stronger tube material, such as stainless steel, may be required. As for the manufacture of the catheter assembly, the various parts can be readily manufactured by a variety of molding procedures, such as extrusion molding, well known in the art.

Preferably, the liquid is delivered by means of a syringe through a sterile port at the proximal section of the second tube. The proximal end may also house a positive end expiratory pressure valve, which momentarily inhibits expiration, thereby increasing the alveolar pressure and providing a greater diffusion capacity.

The liquid therapeutic agent delivered may include water or a saline solution for lavage purposes, medications, including catecholamines such as epinephrine, anticholinergics such as atropine, anesthetics such as lidocane, any of a variety of well known selective β-2 agonists, antioxidant medications, broncho-dilators, etc. Other liquid therapeutic agents delivered may include pulmonary surfactants, such as Exosurf and Neonatal. In any given situation, however, the decision of which liquid to administer will be determined by the health care professional.

The above description of the invention will be made more clear by the examples which follow, which examples are offered by way of illustration, not limitation.

EXAMPLE 1

Comparative Bioequivalency Assays Employing the Catheter Assembly of the Invention And Prior Art Intrapulmonary Drug Delivery Devices An intrapulmonary atomizing device as described above and in the drawings (hereinafter referred to as the Intrapulmonary Medication Aerosolizer, or IMA™) was used in the following experiments, with the entire device being integrally associated with an endotracheal tube, and modified for dogs. Comparative experiments were performed using the STD method of intrapulmonary drug delivery, described above, as well as using a "below the cuff" intracatheter device (similar to the Mallinkrodt EMT™ and Autovage® Endoject™ devices, described above). Plasma concentration and mean arterial pressure response curves to epinephrine delivered endotracheally were compared during resuscitation from a beta-blocker overdose. Four anesthetized dogs were placed in multiple chemically-medicated acute hypotensive crisis for five minutes. Epinephrine was then introduced into the lungs, at 20 ug/kg using the devices. Plasma samples and mean arterial pressures were obtained from the proximal aorta for controls, at pharmacodynamically critical times to determine bioequivalency.

Animal Preparation

Six heart worm-free adult female dogs (Hound) weighing 26 to 35 kg. were fasted for 12 hours prior to experimentation. An intravenous (I.V.) infusion of normal saline was established by the peripheral puncture of a leg vein with a 20 gauge teflon catheter. The dogs were anesthetized with sodium pentobarbital I.V. (22 mg/kg), then intubated with the same 8.0 mm inner diameter device as described in FIG. 1. The dogs were maintained under anesthesia with 1–2.5% isoflurane in oxygen. A surgical cut down was performed in the internal carotid artery, and a 16 cm #20 polyethylene catheter was inserted into the lumen of the proximal aortic arch. The aortic catheter was used for recording mean arterial pressure and plasma sampling. The aortic catheter was connected to a Physiograph for data recording. Heart rate and cardiac rhythm was monitored by a standard ECG (lead two).

Experimental Protocol.

The animal model was designed to mimic the physiological environment found in human cardiac arrest patient with CPR in progress. The model uses a beta-blocker induced inotropic or chronotropic insult by administrating Esmolol (average dose 5 mg/20 min.). The dogs were then stabilized in this state (infusion of 1,250 micrograms/min. Esmolol) for 5 minutes to allow endogenous catecholamine (epinephrine) levels to rise in response to the acute systemic hypotension.

Ten beta-blocker (Esmolol) overdoses were induced in each dog in the assays involving the below the cuff device, two of which were controls. For the experiments involving the STD method and the IMA™ device of the invention, the number of trials was 18 with two controls. In the controls, physiological responses and plasma samples were obtained but treatment was withheld.

Plasma catecholamine levels were obtained prior to each Esmolol administration for the controls. Baseline plasma catecholamine levels were drawn at T=0 min. when the beta-blocker was discontinued. At T+0 min., 20 micrograms/kg of epinephrine in 7 ml saline was given via the device, with a 3 ml saline flush to evacuate epinephrine residuals in the medication conduit. Ventilation rates were artificially maintained by a ventilator (16/min. volume 0.81, 80% oxygen, 1–2.5% isoflurane). Some ventilation conditions were modified to resolve transient minor pulmonary edema from pulmonary hypertension. Blood was drawn after the saline flush at T=1, 2.5, 5, 10 and then at 30 and 45 minutes (3 ml sample). Mean arterial pressure was recorded at T=0 and then every minute for the first ten minutes, then every five minutes up until 45 minutes. blood sugar was checked after each hypotensive episode to detect critical fluctuations (dextrose-stick). All blood sugar levels were within normal limits. Time intervals of ten minutes were interspersed between trials to allow for epinephrine metabolism and animal recovery. Hematocrit was also checked, due to multiple blood draws. This procedure affirmed that the blood volumes were not comprised. Equal volumes of normal saline were replaced during the rest periods.

Sample Collection

Plasma epinephrine blood samples were drawn from the proximal aorta at the aforementioned times, and the blood was placed into test tubes containing EDTA. The samples were centrifuged and the plasma was placed into polyvinyl microtubes containing 200 microliters of 0.05M glutathione. The samples were then mixed and quickly placed in an ultra-low freezer at −80 degrees Centigrade.

Blood Plasma Catecholamine Measurements

To assay the plasma epinephrine samples, the catecholamine was separated from the sample matrix by adsorption onto alumina, extracted with 0.1M perchloric acid and quantified by HPLC. Dihydroxybenzylalamine (DHBA) was used as the internal standard. The HPLC system was a Bioanalytical Systems (BAS) liquid chromatograph with an aperometric detector (LC17,LC4A). Strawberry Tree Workbench PC 2.04 software was used on an IBM compatible PC for data collection and integration. All conditions conformed to current literature and standards.

Figure 15:
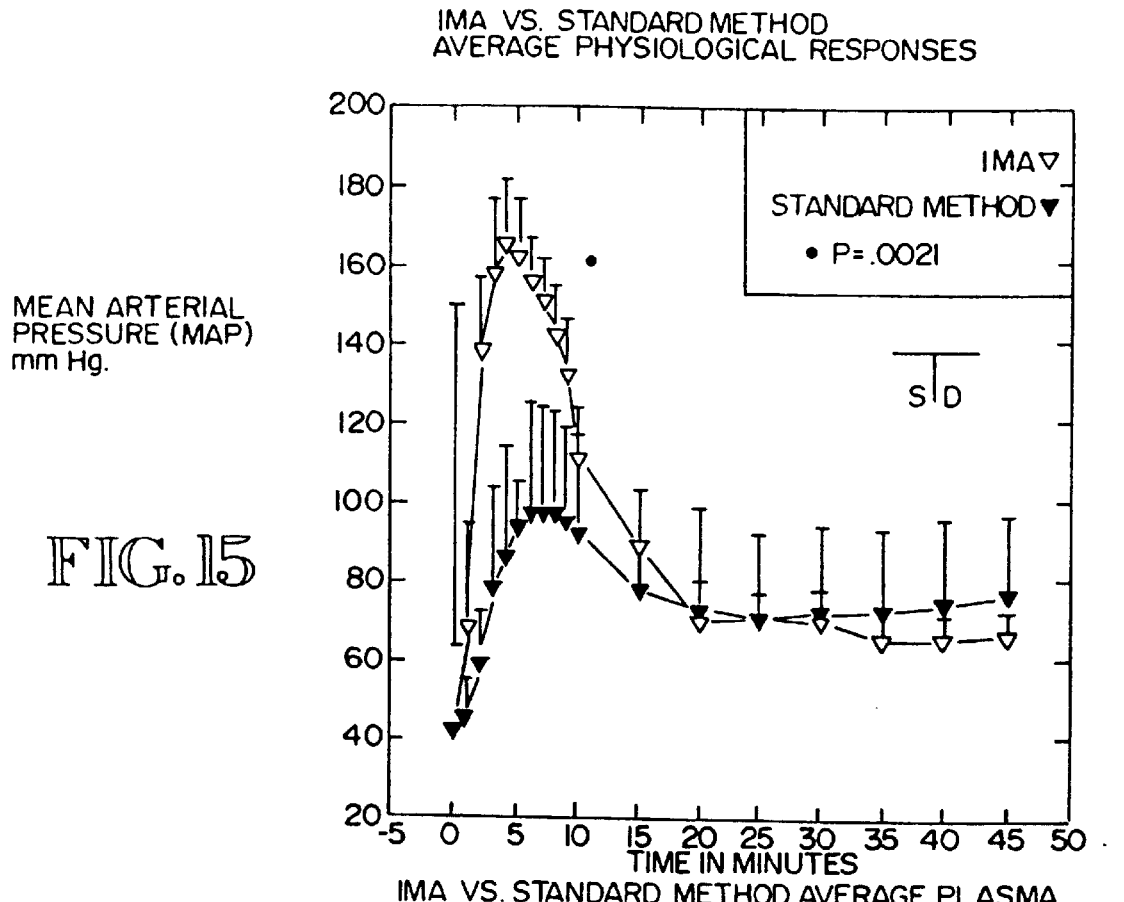
FIG. 15 is a graph showing how physiological responses to a selected drug, change as a function of time after administration of the drug using a prior art device, versus the invention.
Figure 16:
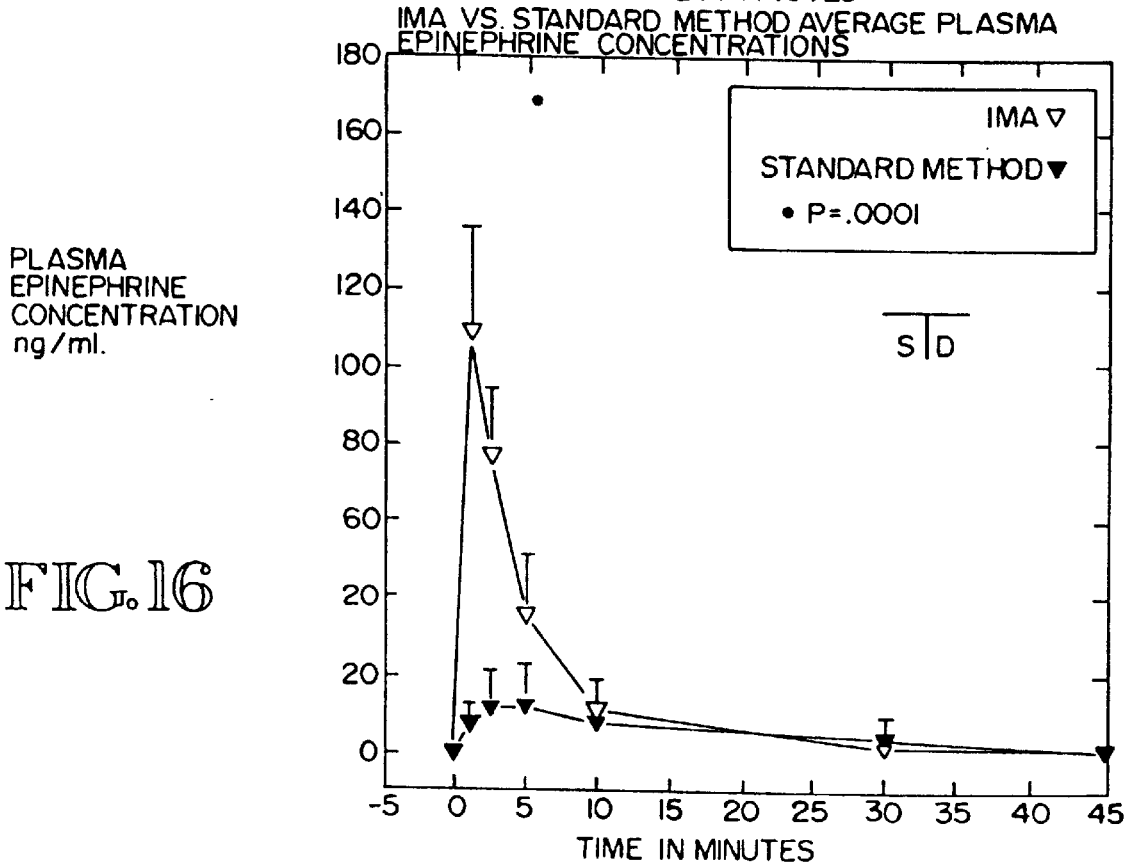
FIG. 16 is a graph showing how plasma concentration of a selected drug changes as a function of time after administration of the drug using prior art devices, versus the invention.

The plasma and physiological data were analyzed using repeated measures analysis of variance (ANOVA), and the pooled data are presented graphically in FIGS. 14–16. The variability between data points was divided into variability between.

Within this cardiac arrest model, the IMA device proved to be effective in delivering epinephrine to the respiratory tissues. The beta blocker overdose did not significantly effect the physiological response to epinephrine between repeated tests and between dogs. The IMA device was shown to deliver a bolus dose of epinephrine, substantially equivalent to an intravenous dose delivery, and unlike an infusion delivery. Indeed, the IMA dose was bioequivalent to an intravenous dose in terms of its absorption and physiological activity, as was shown by the rapid plasma concentration changes and systemic physiological responses, coupled with the inverse responses after T=10 minutes.

Referring to FIGS. 14 and 16, at T=1 minute the IMA exhibited an average 14 fold increase in concentration over the STD and below the cuff methods. At the time of epinephrine's peak effect (T=2.5 min.), the IMA exhibited an average 6.5 fold increase in plasma epinephrine concentration over the STD method, and a comparable increase over the below the cuff method. At T=10 minutes the IMA plasma epinephrine levels are on the average 0.4 times higher than STD methods. At T=30 minutes the STD plasma epinephrine concentrations are on the average 2.5 times higher than the IMA, and at T=45 minutes the STD method exhibited an average 0.68% increase in concentration over the IMA, indicating that adverse pooling bad occurred in the STD trials.

Comparing FIGS. 14, 15 and 16, all of the plasma epinephrine concentration data appear to be in direct proportion to the physiological data for the IMA, indicating that the device of the invention is at least bioequivalent, if not more effective, in terms of dose delivery compared to intravenous delivery. In particular, the IMA mean arterial pressure (MAP) data demonstrate that there is a very rapid and strong physiological response to epinephrine administered through the IMA. The peak MAP response coincides with epinephrine's peak effect time (1–2.5 minutes). The IMA MAP data also demonstrate that at ten minutes there is a significant drop in the MAP, which corresponds to epinephrine's period of action (10 min.).

The MAP data for the STD method demonstrates a significantly slower and weaker response to epinephrine. The peak MAP response is 3.5 to 5.5 minutes after epinephrine peak effect time. The relative drop at ten minutes is also smaller.

According to the control data the physiological responses are from the epinephrine not from the cessation of the B-blocker overdose. The control data suggest that return to normotension occurs around 30 to 35 minutes and that there was no significant physiological response change between controls one and ten and controls between dogs (P=0.1353) (FIGS. 2, 3). The IMA and STD data exhibit periods where the MAP falls below that of the control data (T=15–45 min.). It is well documented that as the systemic response to epinephrine wanes the MAP falls below normal before returning to control.

The plasma and physiological data were analyzed using repeated measures analysis of variance. Within this cardiac arrest model, the IMA device proved to be significantly more effective and less variable than the current intrapulmonary methods of delivering epinephrine into the systemic circulation (Plasma P=0.0001) (MAP P=0.0021). Comparing the IMA and STD methods in the critical first ten minutes, the IMA demonstrates extreme significance in rate and size of MAP and plasma concentration response (P=0.0001) (FIG. 10).

EXAMPLE 2

Based on bio-equivalancy results presented in the previous example, it is likely that the IMA is actually more effective in delivering medications to the systemic circulation than the intravenous method. To test this hypothesis the proposed experiments will employ a canine cardiac arrest model. The arrest model will be rigorous in its length of arrest and thus accurately model zero blood flow conditions found in cardiac arrest patients. The studies will examine central and peripheral plasma epinephrine and lidocaine levels following exogenous administration, using the IMA and standard peripheral IV methods.

These experiments will measure the following independent variables: Coronary perfusion pressure (CPP), end-diastolic pressure, right atrial pressure, pulmonary perfusion pressure, regional pulmonary blood flow, pulmonary microvascular blood flow, central venous pressure (CVP), cerebral perfusion pressure, blood glucose, expiratory $CO_2$, bilateral pulmonary and peripheral venous blood gas, peak airway pressure, post resuscitation CNS function.

Animal Preparation

Thirty two heart worm free adult dogs (Hound) weighing 20–25 kg. will be fasted for 12 hours prior to experimentation, with free access to water. An I.V. infusion of normal saline will be established by the peripheral puncture of a leg vein with a 20 g. Teflon catheter. The dogs will be anesthetized with sodium pentothol I.V. (22 mg/kg). Upon reaching stage III plane 2 of surgical anesthesia the dogs will be intubated with an ETT and mechanically ventilated on a time cycled volume controlled ventilator (rate 14/min, $V_T$15 ml/Kg). The dogs will be anesthetically maintained on 0.75–2.0% isoflurane in oxygen for maintenance of surgical anesthesia and suppression of corneal reflexes. Four dogs will be used for control and practice of experimental method.

Instrumentation

A surgical cut down will be performed on the left internal carotid artery, and a 16 cm #20 polyethylene catheter will be inserted in to the lumen of the proximal aortic arch. The aortic catheter will be used for recording mean diastolic aortic pressure and plasma sampling. A second catheter will be placed in the proximal caudal branch of the right femoral artery for continuous systemic blood pressure recording. Heart rate and cardiac rhythm will be monitored by a standard ECG (lead two). Two venous catheters will be established. One through the left internal jugular to the right atrium for plasma sampling and for mid-diastolic right artrial pressure. A second venous catheter will be placed in a peripheral leg site for plasma sampling. Transonic Systemic Inc. (TS) absolute blood flow probes will be placed at the pulmonary artery bifurcation one on each (R, L) artery. TS probes will also be placed on the major branches of the (R, L) pulmonary veins. Two TS microvascular perfusion probes will be placed on each lung on the ventral and dorsal surfaces. The TS absolute flow probes will measure regional pulmonary blood flow and the microvascular probes will measure capillary blood flow. All physiological data will be recorded and integrated real time by a Strawberry Tree™ Workbench data acquisition board connected to a PC.

A thoracotomy and a pericardiectomy will be performed at the left fifth intercostal space to provide direct access for initiation of cardiac arrest and circumferential cardiac compression during resuscitation. Proper placement of all thoracic catheters and probes will be checked by means of direct visualization and palpitation.

Postmortem the distal trachea will be excised around the area of the carina. The tissue will be examined on the gross and histological levels. Specimens will be placed in 10% formalin for 24–48 hours, processed and embedded in paraffin. The specimens will then be cut into 5 um. sections and stained with H & E. The sections will be examined for microscopic cellular damage, which would indicate local injury caused by the IMA delivery mechanism.

Cardiac Arrest

Initiation of cardiac arrest will begin with direct fibrillation of the heart by delivering a 10–15 s, 60 Hz, 2 ms square-wave stimulus to the left ventricular epicardium. Ventilation will be discontinued and circulatory arrest will be confirmed by ECG, MAP and direct observation of the heart.

Resuscitation

After 8 minutes of nonintervention, blood will be drawn for plasma catecholamine control and resuscitation efforts will begin. At T=8.0 min., ventilation with 80% $O_2$ and direct cardiac massage will be performed to maintain CPP between 15–20 mm Hg. Ventilation to compression ratio will be approximately 1:5. At T=8.5 minutes, 40 ug/kg of epinephrine will be administered using either the IMA or the IV method (randomized). At T=10.5 minutes 1 mg/kg Lidocaine in 10.0 ml N.S. will be administered using either the IMA or the IV method.

During medication delivery, two different ventilatory methods will be examined. The dogs will be placed into two groups n=14 (IMA and IV). Each groups will be further divided into two ventilation subgroups n=7 (Normal and Positive End Expiratory Pressure, PEEP=5.0 cm $H_2O$). After medication delivery ventilation will be time cycle controlled (rate 14 min, $V_T$ 15 ml/Kg, 0.75–2.5% isoflurane).

Blood will be obtained for plasma catecholamine and lidocaine analysis from the proximal aorta, right atrium, right and left pulmonary veins and peripheral venous vasculature at the following times: Time=every ½ minute to the 10 minute mark, then every five minutes to 30 minutes, then every 10 minutes until T=1.0 hour. Blood gases will be obtained from the left and right pulmonary veins and a peripheral venous site every two minutes until T=10 minutes. Then every 5 minutes until T=30 minutes. Then every 10 minutes until 1.0 hours. Then at each neurological exam, from a peripheral site. Total blood sampling will be <5.9% of total circulating blood volume. The aforementioned physiological responses will be recorded and integrated real time.

Immediately after T=14.5 after 6.0 minutes of direct cardiac massage and ventilation, the heart will be directly cardioverted by delivery of a 20–50 Joule charge with 31 $cm^2$ paddles placed on the right and left ventricular surfaces. More vigorous direct cardiac massage and additional ACLS medication (except epinephrine and Lidocaine) and charges will be delivered as necessary to increase MAP and CPP to normal levels. At T=15 minutes if the MAP<75 mm Hg or the CPP is <35 mm Hg, dopamine at 15 ug/(Kg*min) will be peripherally infused. Dopamine should not obscure the quantitative analysis of epinephrine.

Resuscitated dogs will be placed in a simulated cardiac care unit (CCU) environment for two hours to monitor immediate cardiovascular stability. Anesthesia will be continued with 50% isoflurane and 50% oxygen. Standard cardiac drugs and fluids will be employed to maintain MAP of 80 to 120 mm Hg. Each dog will receive penicillin G 500,000 units IM. At one and a half hours, neostigmine will be given to reverse paralysis and the dogs will be weaned from the ventilator.

In the weaned dogs catheters will be removed and treated locally with 10 ml of 0.25% bupivicaine. A peripheral catheter will be maintained with a heparin lock. At 2, 4, 8, 12 and 24 hours a standard neurologic examination will be performed. If behavior indicative of pain or agitation is noted, morphine sulfate 2 mg boluses will be given until the dog appears comfortable.

The Neurological Deficit Scale (NDS) is divided as follows 1) level of consciousness, 2) respiratory abnormalities, 3) cranial nerve deficits, 4) motor deficits, 5) behavior deficits. The maximum deficit in each category represents a score of 100 points. The total neurological deficit score ranges from 500 (brain dead) to 0 (Normal).

Upon completion of the experiment, the dogs will be euthanized (Panel on Euthanasia of the American Veterinary Medical Association).

Sample Collection

Blood samples will be drawn from the proximal aorta, right and left pulmonary veins, right atrium and at a peripheral site at the aforementioned times, blood will then be placed into test tubes containing EDTA. The samples will be centrifuged and the plasma placed into polyvinyl microtubes containing 200 ul. of 0.05M glutathione. The samples will then be mixed and quickly placed in an ultra-low freezer at −70 C.

Catecholamine Measurement

Plasma epinephrine will be separated from the sample matrix by adsorption on to alumina, extracted with perchloric acid and quantified by HPLC. Dihydroxybenzylalamine (DHBA) will be used as the internal standard. The HPLC system will be a Bioanalyitical Systems®, West Lafayette, Ind. (BAS LC4C) Liquid chromatograph with an amperometric detector. The column dimensions are, 10 cm.×3.3 mm. Loaded Phase 2 ODS 3 um. A BAS glassy carbon working electrode will be used at +650 mV potential with a Ag/AgCI reference electrode. StrawberryTree WorkBench for Windows™ software will be used on a IBM compatible PC for data collection and integration. Mobile Phase: Sodium phosphate monobasic, heptane sulfuric acid, EDTA and methanol, adjusted to pH 3.60. An isocratic flow will be maintained at 0.8 ml/min.

Plasma will be thawed, and along with standard solutions subjected to a standard alumina assay procedure. epinephrine will be eluted with perchloric acid and then 50 ul. of the eluate will be injected into the BAS 200.

epinephrine in each 50 ul. sample will be calculated from linear regression analysis of a standard curve constructed by addition of an internal standard (DHBA) to known amounts of epinephrine. The known amounts will then be run through the sample preparation and HPLC.

Lidocaine Measurement

Plasma Lidocaine will be quantified by luminescence spectroscopy using the Syva emit lidocaine assay procedure. 200 ul. of plasma will be placed into polyvinyl tubes containing reagent and placed into a Perkin Elmer luminescence spectrometer LS 50. Strawberry Tree WorkBench for Windows™ software will be used on a IBM compatible PC for data collection and integration.

Data Analysis:

Statistics will be generated using a one way analysis of variance (ANOVA) with Bonferroni's correction for multiple comparisons. The variability between the data points will be divided into variability between the groups (IV/IMA) (Normal/ PEEP) and the variability within groups (residual, presumed to be random) will test the null hypothesis that the population means will be equal within groups using the P=0.05 level of significance.

Those with ordinary skill in the art will appreciate that other embodiments and variations of the invention are possible which employ the same inventive concepts described above. Therefore, the invention is not to be limited except by the above description, but is to be determined in scope by the claims which follow.

I claim:

1. An endotracheal catheter assembly for intrapulmonary transfer of liquid drugs and other liquid therapeutic agents in a mammalian patient, comprising:

a first tube having a first outer wall, a first inner wall, a first lumen, at least one first proximal section and at least one first distal tip, said first tube having a length suitable for endotracheal insertion of said first tube in an airway of the patient to position said first distal tip near a carina of said patient;

a second tube of approximately the same length as said first tube, said second tube having a second outer wall, a second inner wall, a second lumen, at least one second proximal section, and at least one second distal tip, said first and second distal tips arranged to form at least one nozzle, said nozzle defining a high velocity gas/liquid interface formed between the first and second distal tips characterized by the first lumen having a comparative cross-sectional area relative to a cross-sectional area of said second lumen, at a position of said nozzle, of between approximately 0.4:1.0 and 4.0:1.0;

gas receiving means connected to said first tube at or near said first proximal section is gaseous connection with said first lumen to allow transfer of gas to and from said first lumen; and liquid receiving means connected to said second tube at or near said second proximal section in liquid connection with said first lumen, to allow transfer of liquid to and from said first lumen.

2. A catheter assembly according to claim 1, wherein said cross-sectional area of said first lumen relative to said cross-sectional area of said second lumen at said position of said nozzle is between approximately 1.0:0.6 and 2.0:1.0.

3. A catheter assembly according to claim 1, wherein said cross-sectional area of said first lumen relative to said cross-sectional area of said second lumen at said position of said nozzle is between approximately 0.9:1.0 and 1.0:1.0.

4. A catheter assembly according to claim 1, wherein said first tube has an inner diameter of between approximately 0.018 cm and 0.480 cm, and said second tube has an inner diameter of between approximately 0.016 cm and 0.184 cm.

5. A catheter assembly according to claim 1, wherein said first tube has an inner diameter of between approximately 0.027 cm and 0.240 cm, and said second tube has an inner diameter of between approximately 0.024 cm and 0.090 cm.

6. A catheter assembly according to claim 1, wherein said first tube has an inner diameter of between approximately 0.114 cm and 0.122 cm, and said second tube has an inner diameter of between approximately 0.040 cm and 0.048 cm.

7. A catheter assembly according to claim 1, wherein said second tube is nested within said first lumen between said first proximal section and first distal tip, so that gas passes unobstructed between said first inner wall and said second outer wall and a circumferential high velocity gas/liquid interface is created at said nozzle when high velocity gas exits said first distal tip and liquid exits said second distal tip.

8. A catheter assembly according to claim 1, wherein said first tube and said second tube form part of a single, bi-lumenal catheter, the first tube and second tube being separated by a longitudinal septum of said cathether separating said first and second lumens and joined to said first and second inner walls, so that a high velocity gas/liquid interface is created adjacent said septum at said nozzle when high velocity gas exits said first distal tip and liquid exits said second distal tip.

9. A catheter assembly according to claim 1, further comprising coupling means for coupling said catheter assembly to a standard, ventillatory endotracheal tube, said coupling means adapted to permit sealable insertion of said first tube of said catheter assembly within a lumen of said endotracheal tube.

10. A catheter assembly according to claim 9, wherein said coupling means includes a standard ventilator connector for connecting an endotracheal tube to a ventilator, said ventilator connector modified to include a sealable catheter port for sealably receiving said first tube of said catheter assembly through said port and into said lumen of said endotracheal tube when a proximal end of said endotracheal tube is connected to said ventilator connector.

11. A catheter assembly according to claim 9, further comprising means for selectably, lockably repositioning said first tube of said catheter assembly longitudinally within said lumen of said endotracheal tube to permit selectable, lockable repositioning of said nozzle of said catheter assembly relative to a distal tip of said endotracheal tube.

12. A catheter assembly according to claim 11, wherein said means for selectably, lockably repositioning said first tube and second tube of said catheter assembly longitudinally within said lumen of said endotracheal includes an adjustable, compressible sleeve adjustably compressible against said first outer wall.

13. A catheter assembly according to claim 1, further comprising a standard, ventillatory endotracheal tube, and coupling means for coupling said catheter assembly to said endotracheal tube, said coupling means adapted to permit sealable insertion of said first and second tubes within a lumen of said endotracheal tube.

14. A catheter assembly according to claim 1, further comprising an axial orientation marker visible on said assembly when said assembly is endotracheally inserted, wherein said first and second distal tips each bifurcate to form two nozzles, so that each of said nozzles can be orientated to each point in a direction of one lung of normal physiology when said nozzles are positioned near said carina.

15. A catheter assembly according to claim 1, wherein said nozzle has two, bilateral hemi-nozzles, and wherein said catheter assembly has an axial orientation marker visible on said assembly when said nozzle is endotracheally inserted, whereby the hemi-nozzles can be orientated by a caregiver to each point in a direction of one lung of normal physiology when said nozzle is positioned near said carina.

16. A catheter assembly according to claim 1, wherein said catheter assembly has a longitudinal orientation marker visible when said first tube is partially endotracheally inserted, so that said nozzle can be longitudinally positioned by a caregiver near said carina.

17. A catheter assembly according to claim 1, wherein said second tube is removably nested within said first lumen, so that the high velocity gas/liquid interface formed between the first and second distal tips at the nozzle is circumferential relative to the second distal tip, and said second tube can be removed from said first tube to enlarge said first lumen and to adapt said first tube for multi-purpose use.

* * * * *